United States Patent
Han

(10) Patent No.: US 10,595,962 B2
(45) Date of Patent: Mar. 24, 2020

(54) ULTRASONIC ENDODONTIC SURGICAL INSTRUMENT

(71) Applicant: Han Instruments, LLC, Westlake Village, CA (US)

(72) Inventor: David C. Han, Encino, CA (US)

(73) Assignee: HAN INSTRUMENTS, LLC, Valencia, CA (US)

( * ) Notice: Subject to any disclaimer, the term of this patent is extended or adjusted under 35 U.S.C. 154(b) by 287 days.

(21) Appl. No.: 15/725,581

(22) Filed: Oct. 5, 2017

(65) Prior Publication Data

US 2018/0280114 A1  Oct. 4, 2018

Related U.S. Application Data

(60) Provisional application No. 62/481,342, filed on Apr. 4, 2017.

(51) Int. Cl.
| | |
|---|---|
| A61C 5/00 | (2017.01) |
| A61C 5/42 | (2017.01) |
| A61C 1/07 | (2006.01) |
| A61C 3/03 | (2006.01) |

(52) U.S. Cl.
CPC .................. *A61C 5/42* (2017.02); *A61C 1/07* (2013.01); *A61C 3/03* (2013.01)

(58) Field of Classification Search
CPC .... A61C 5/42; A61C 1/07; A61C 5/46; A61C 5/40
USPC ....................................................... 433/102
See application file for complete search history.

(56) References Cited

U.S. PATENT DOCUMENTS

| | | | |
|---|---|---|---|
| 4,571,183 A * | 2/1986 | Nash ................ | A61B 17/1624 433/116 |
| 5,752,825 A * | 5/1998 | Buchanan ............ | A61C 5/42 433/32 |
| 6,267,594 B1 * | 7/2001 | Hugo ................. | A61B 17/1637 433/119 |
| 6,387,035 B1 | 5/2002 | Jung, Jr. et al. | |
| 6,716,028 B2 * | 4/2004 | Rahman .............. | A61C 1/07 433/119 |
| 7,967,816 B2 | 6/2011 | Ocel et al. | |
| 2002/0127512 A1 * | 9/2002 | Chen ................... | A61C 1/07 433/119 |
| 2002/0142261 A1 * | 10/2002 | Van Den Houdt ..... | A61C 5/40 433/81 |

(Continued)

OTHER PUBLICATIONS

ProUltra-Endo-Tips, Dentsply Sirona, York, PA, 2012.

(Continued)

*Primary Examiner* — Nicholas D Lucchesi
(74) *Attorney, Agent, or Firm* — SoCal IP Law Group LLP; Guy Cumberbatch; Steven C. Sereboff

(57) ABSTRACT

An ultrasonic root end retro-preparation endodontic apical surgical instrument. The instrument has a double-angled shape with a length of between about 1-2 in (2.5-5.1 mm), and is made of a metal which safely and effectively propagates ultrasonic energy from a base segment to a bent distal tip with a length of between about 0.08-0.15 in (0.20-0.38 mm). The instrument includes a swivel segment that permits rotation of the bent distal tip of up to 360°. By allowing the bent distal tip to be swiveled, the instrument may be used for all quadrants, anterior and posterior teeth without switching out the instrument for another one.

20 Claims, 4 Drawing Sheets

(56) References Cited

U.S. PATENT DOCUMENTS

| | | | |
|---|---|---|---|
| 2004/0126735 A1* | 7/2004 | Hickok | A61C 1/07 433/119 |
| 2005/0032017 A1* | 2/2005 | Levy | A61C 1/07 433/29 |
| 2007/0015108 A1* | 1/2007 | Ruddle | A61C 1/07 433/122 |
| 2008/0248444 A1 | 10/2008 | Bahcall et al. | |
| 2011/0039234 A1* | 2/2011 | Huber | A61C 3/02 433/224 |
| 2011/0256505 A1* | 10/2011 | Buchanan | A61C 17/0202 433/166 |
| 2012/0214125 A1* | 8/2012 | Clark | A61C 5/42 433/102 |
| 2013/0123774 A1* | 5/2013 | Zadeh | A61B 17/16 606/39 |
| 2014/0113246 A1* | 4/2014 | Jaramillo | A61C 3/00 433/102 |
| 2015/0150647 A1* | 6/2015 | Chevalier | A61C 3/02 433/27 |
| 2017/0071710 A1* | 3/2017 | Deturmeny | A61C 17/02 |
| 2018/0125622 A1* | 5/2018 | Almoumen | A61C 17/0202 |
| 2018/0214247 A1* | 8/2018 | Sharma | A61C 5/50 |

OTHER PUBLICATIONS

Hu-Friedy Ultrasonic Scaling Brochure, Hu-Friedy Mfg. Co., Chicago, IL, ©2011.
SybronEndo Ultrasonic Tips Brochure, Sybron Dental Specialties, Orange, CA, 2010.

* cited by examiner

ULTRASONIC ENDODONTIC SURGICAL INSTRUMENT

CROSS-REFERENCE TO RELATED APPLICATIONS

This application claims the benefit of priority under 35 U.S.C. § 119 to U.S. Provisional No. 62/481,342, filed Apr. 4, 2017.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

FIELD OF THE INVENTION

The disclosure relates to an ultrasonic root end retro-preparation endodontic apical surgical instrument.

BACKGROUND OF THE INVENTION

Endodontic therapy or root canal therapy is a sequence of treatment for the infected pulp of a tooth which results in the elimination of infection and the protection of the decontaminated tooth from future microbial invasion. Root canals, and their associated pulp chamber, are the physical hollows within a tooth that are naturally inhabited by nerve tissue, blood vessels and other cellular entities. Together, these items constitute the dental pulp. Endodontic therapy involves the removal of these structures, the subsequent shaping, cleaning, and decontamination of the hollows with small files and irrigating solutions, and the obturation (filling) of the decontaminated canals.

The success rate of conventional endodontic therapy is 85-95%. If conventional endodontic treatment is unsuccessful, non-surgical root canal retreatment will eliminate the problem. If retreatment of root canal is not possible because of natural, restorative or iatrogenic obstructions, endodontic surgery is indicated. Root-end surgery includes surgical debridement of pathological peri-radicular tissue, root-end resection, root-end cavity preparation and filling of the root-end cavity to seal the root canal effectively.

Traditionally, the root-end cavity is prepared with burs used with low-speed handpiece. Cavity preparation with burs has some disadvantages including limited operative field and root-end bevel, which increases the number of exposed dentinal tubules on the root-end surface. Ultrasonic surgical tips have been introduced as an alternative to the burs for root-end cavity preparation, and was able to solve some of these problems. Ultrasonic root-end preparation allows cleaner and deeper cavity centered in the root canal and reduced bevel angle.

There are several ultrasonic surgical tips with different shapes and sizes. Early tips were made of stainless steel, and some have special surface coatings to increase their cutting efficiency. Diamond-coated ultrasonic tips are very efficient for removing gutta-percha from the root-end cavity. Also, zirconium-nitride-coated tips are very efficient and provide good vision. Examples of such ultrasonic tips include KiS tips from Kerr Dental of Orange, Calif., and ProUltra ENDO ultrasonic instruments from Dentsply Sirona of York, Pa.

Despite advances in the field, there remains a need for an ultrasonic root end retro-preparation endodontic apical surgical instrument which is easier to use and more effective.

SUMMARY OF THE INVENTION

The present application discloses an ultrasonic root end retro-preparation endodontic apical surgical instrument. The includes a swivel segment that permits rotation of a bent distal tip of up to 360°. By allowing the bent distal tip to be swiveled, the instrument may be used for all quadrants, anterior and posterior teeth without switching out the instrument for another one.

DESCRIPTION OF THE PREFERRED EMBODIMENTS

The present application provides an ultrasonic root end retro-preparation endodontic apical surgical instrument. The instrument attaches onto the hand-piece of all standard endodontic microsurgery ultrasonic units (i.e. mini-Endo, Piezo ultrasonic, P5 Booster Suprasson, etc.).

Figure 1C:
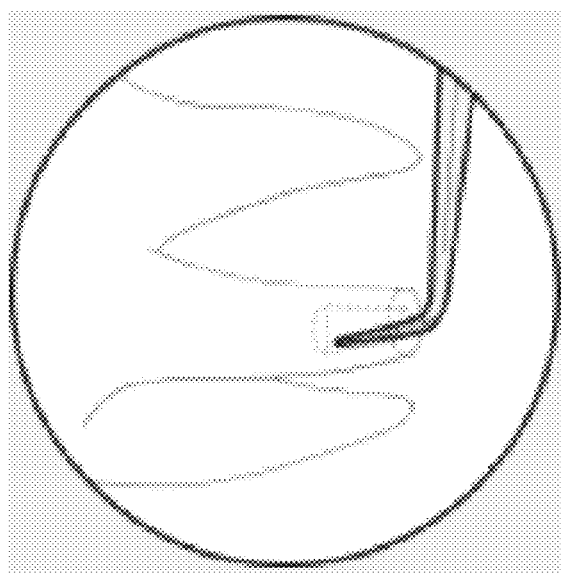
FIGS. 1A-1C are schematic representations of steps in an endodontic root end retro-preparation procedure.
Figure 1B:
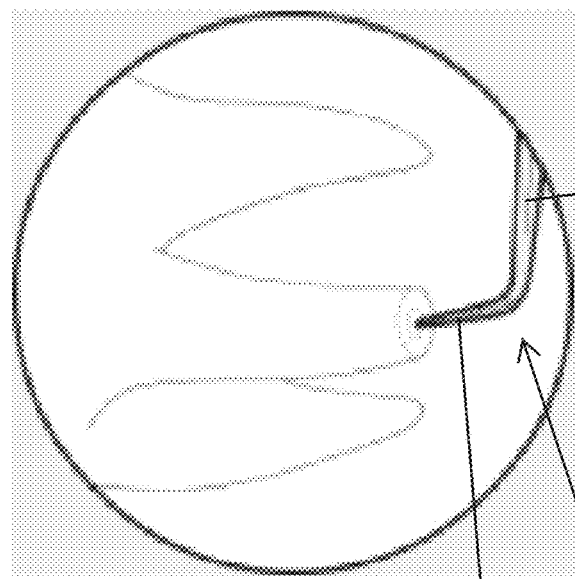
Figure 1A:
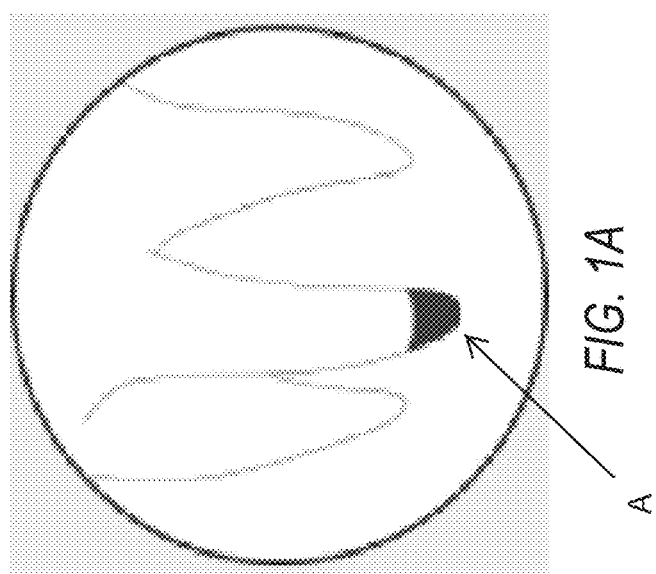

FIGS. 1A-1C are schematic representations of steps in an endodontic root end retro-preparation procedure. A root end retro-preparation procedure may be necessary when root material remains at the apex A of a root canal following a standard approach root canal procedure. Often in such situations, as seen in FIG. 1A, the root material left at the apex A becomes infected causing pain and presenting a risk of broader infection. Consequently, the infected material must be removed from the apex of the tooth root along with apical lateral and delta infected canals.

FIG. 1B illustrates the tooth root after resection of a portion of the apex, exposing the apical end of the root canal. And endodontic instrument 20 having a shaft 22 and a bent tip 24 is then used to access the root canal end. Ultrasonic vibrations imparted to the instrument 20 along with insertion of the bent tip 24 into the root canal, as seen in FIG. 1C, allows the endodontist to thoroughly clean out the infected material.

Figure 2A:
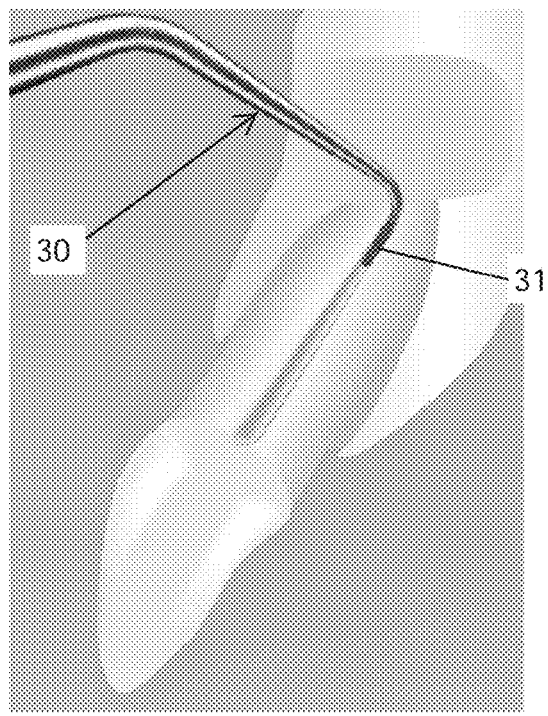
FIGS. 2A and 2B are schematic views of an endodontic root end procedure using different instruments of the prior art.
Figure 2B:
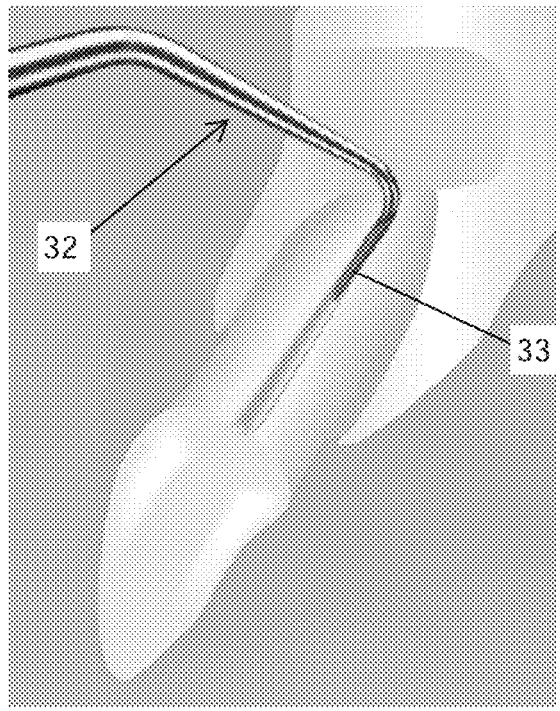

Numerous endodontic instruments for such procedures are known, which creates a problem for the endodontist in tool selection. FIGS. 2A and 2B are schematic views of an endodontic root end procedure on an incisor using different instruments of the prior art. FIG. 2A shows an ultrasonic instrument 30 with a bent tip 31 having a first length, while FIG. 2B shows a similar instrument 32 with a longer bent tip 33.

Figure 3A:
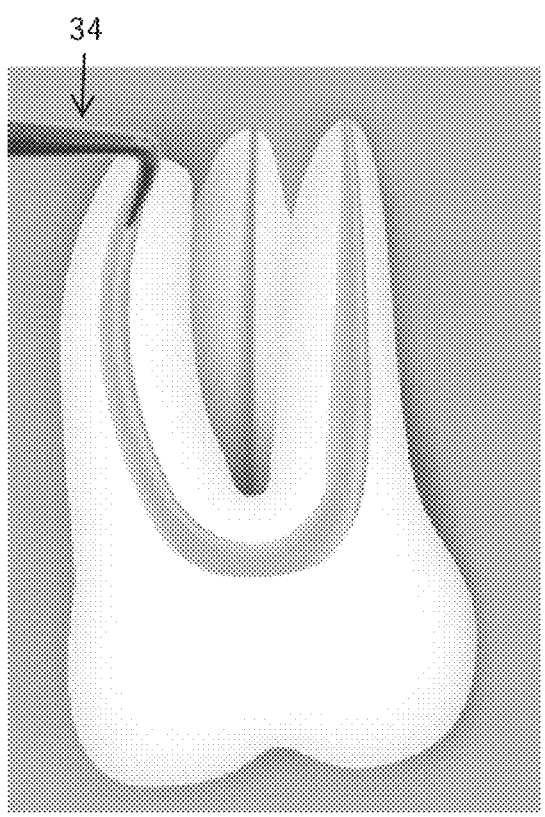
FIGS. 3A and 3B illustrate two different root end endodontic instruments of the prior art having different handed orientations while performing apical approach procedures.
Figure 3B:
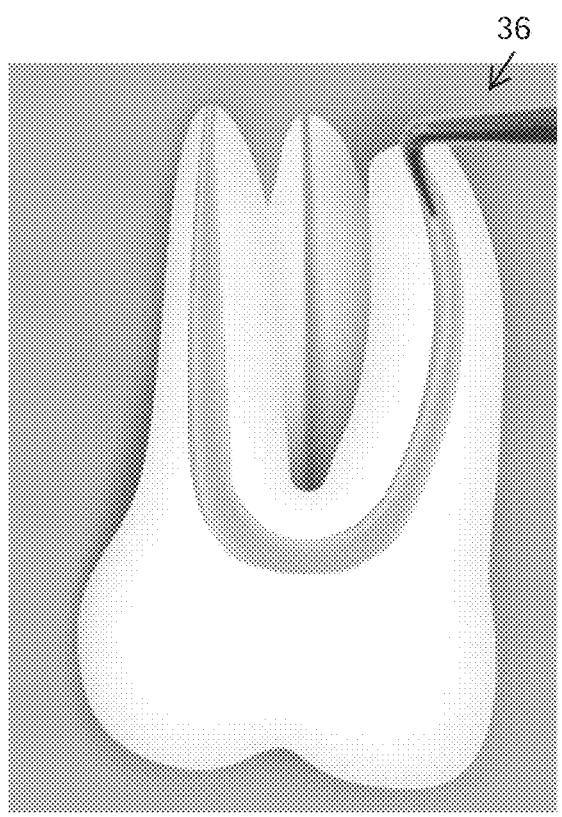

Likewise, FIGS. 3A and 3B illustrate two different root end endodontic instruments of the prior art having different handed orientations. In FIG. 3A, an endodontic root end procedure on a molar is being performed using an ultrasonic tool 34 having a right-handed orientation. Conversely, FIG. 3B shows a similar procedure being performed using an ultrasonic tool 36 having a left-handed orientation.

FIGS. 2-3 illustrate a small selection of the different types of endodontic tools that are available for root end procedures. A search of the field results in a bewildering array of such tools, causing an endodontist to either become educated on the multitudes of tool shapes or rely on the advice of a manufacturing representative. Current tools of this nature have limited angulations, so the endodontist is forced to twist his/her arm and wrist to gain better access in certain quadrants, even if the right handed or left handed oriented instrument is chosen. This is especially true for molar teeth. In most cases, purchase of a large number of tools is required, which can become prohibitively expensive. The present application proposes a different type of endodontic tool which greatly increases the possible uses of the tool and consequently reduces the number of tools needed.

Figure 4B:
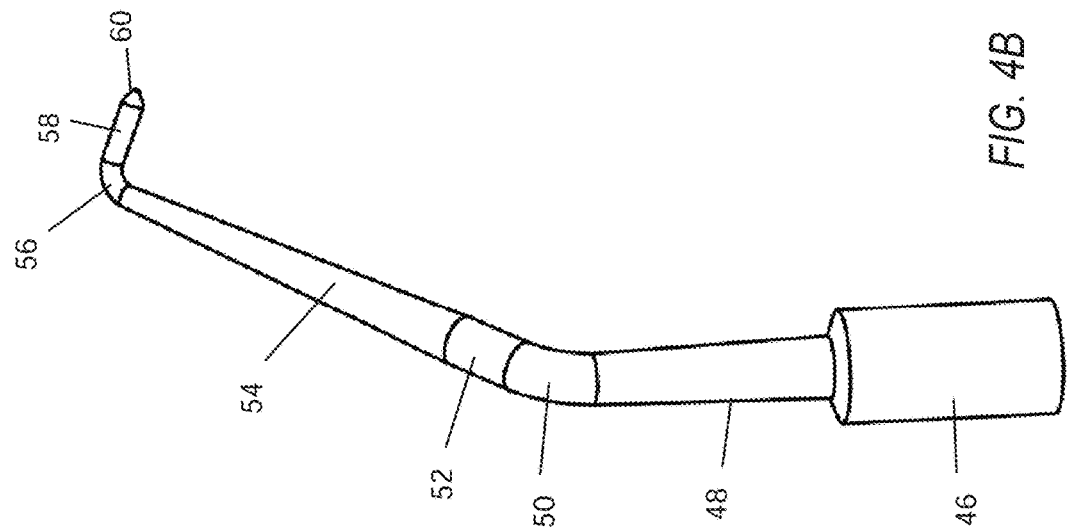
FIGS. 4A and 4B are different perspective views of an exemplary root and endodontic instrument of the present application.
Figure 4A:
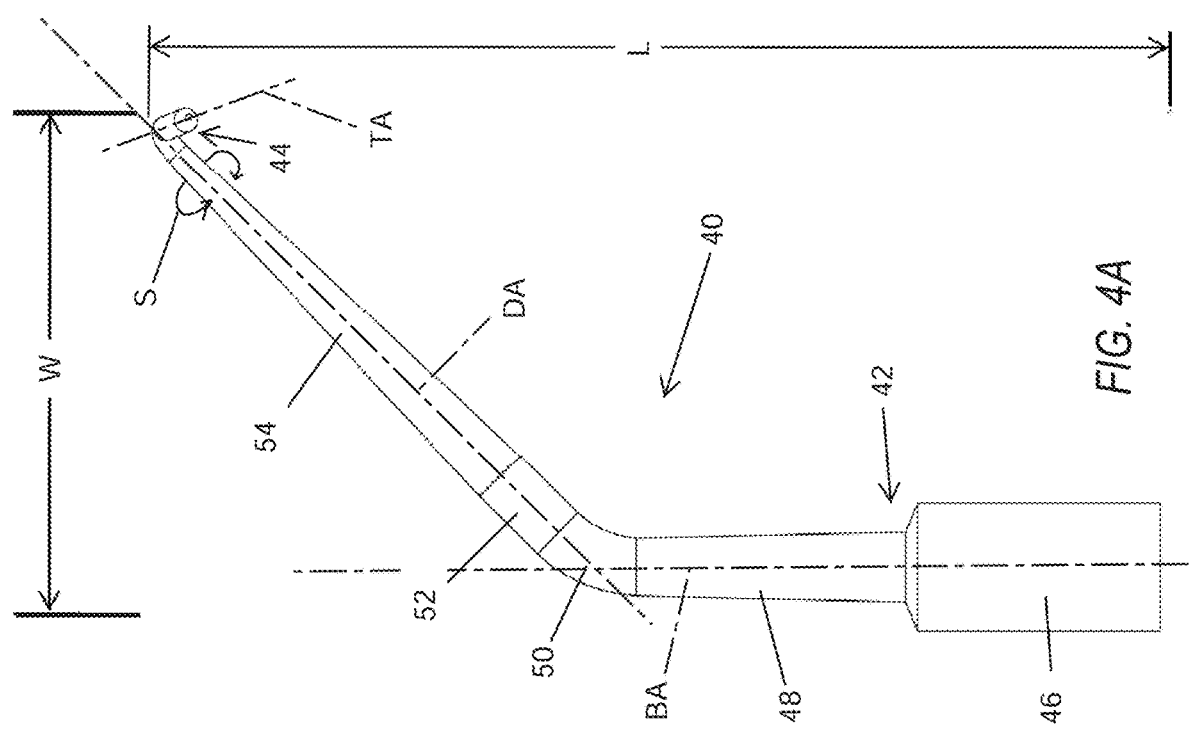

FIGS. 4A and 4B are different perspective views of an exemplary root and endodontic instrument 40 of the present application. The instrument 40 includes a number of different segments from a proximal base 42 to a distal bent tip 44. The base 42 includes a relatively large diameter coupling member 46 and a stepped down shaft portion 48, both concentric about a base axis BA. Both the coupling member 46 and proximal shaft portion 48 preferably have circular cross-sections aligned along a common central axis, with the former having a constant diameter and the latter being slightly tapered. A distal end of the shaft portion 48 connects with a first elbow segment 50 that defines a primary bend of the instrument. The bend may have an angle of between 15-60°, and preferably about 44°.

After the first elbow segment 50, a swivel segment 52 and a distal shaft segment 54 lead to a second elbow segment 56 which is part of the bent tip 44. The swivel segment 52 is desirably cylindrical, while the distal shaft segment 54 is slightly tapered, and both are concentric about a distal axis DA. The bent tip 44 further comprises a straight segment 58 and a pointed distal end 60. The straight segment 58 may be tapered, but preferably has a constant diameter, and defines a tip axis TA. The elbow segment 56 defines a secondary bend such that the intersection of the distal axis DA and the tip axis TA make an angle of between 75-110°, and preferably about 75°. The tool 40 narrows from its proximal base 42 to its distal tip 44, with segments that are either constant diameter (cylindrical) or that taper down.

The swivel segment 52 permits the entire assembly of segments distal thereto to swivel, preferably freely 360° as indicated by the swivel arrow S. Since the distal shaft segment 54 aligns along the same axis DA of the swivel segment 52, it merely rotates about its own axis. However the bent tip 44 can thus be rotated to point in different directions relative to the base 42 and its base axis BA due to the first elbow segment 50. That is, if the plane defined by the distal shaft segment 54 (distal axis DA) and the proximal base 42 (base axis BA) is denoted to be a reference plane, then the plane defined by the distal shaft segment 54 (distal axis DA) and the bent tip 44 (tip axis TA) may be rotated 360° out of that reference plane with the axis DA of the distal shaft segment 54 being common to both planes. More colloquially, if the tool is oriented so that the base axis BA is vertical, as seen in FIG. 4A, the bent tip 44 may be rotated to be angled downward and away from the base axis BA, pointing horizontally to either side, angled upward and toward the base axis BA, and any angle in between.

Although the dimensions of the endodontic tool 40 may vary, its overall dimensions are indicated by an exemplary length L from the proximal end of the base 42 to the bent tip 44, and an exemplary width W primarily defined by the angle of first elbow segment 50 and the length of the distal shaft segment 54, and as measured perpendicular to the base axis BA. In one embodiment, the length L is between about 1-2 in (2.5-5.1 mm), preferably between about 1.2-1.5 in (3.0-3.8 mm), and in one specific embodiment is 1.34 in (3.4 mm). The width W is between about 0.5-1.0 in (1.3-2.5 mm), preferably between about 0.6-0.7 in (1.5-1.8 mm), and in one specific embodiment is 0.62 in (1.6 mm). The length of the bent tip 44 that projects beyond the second elbow segment 56 may vary as well, and is preferably in the range of about 0.08-0.15 in (0.20-0.38 mm). In one specific embodiment, the length of the bent tip 44 is about 0.11 in (0.30 mm). The diameter of the bent tip 44 is desirably between about 0.025-0.035 in (0.06-0.09 mm).

Figure 6:
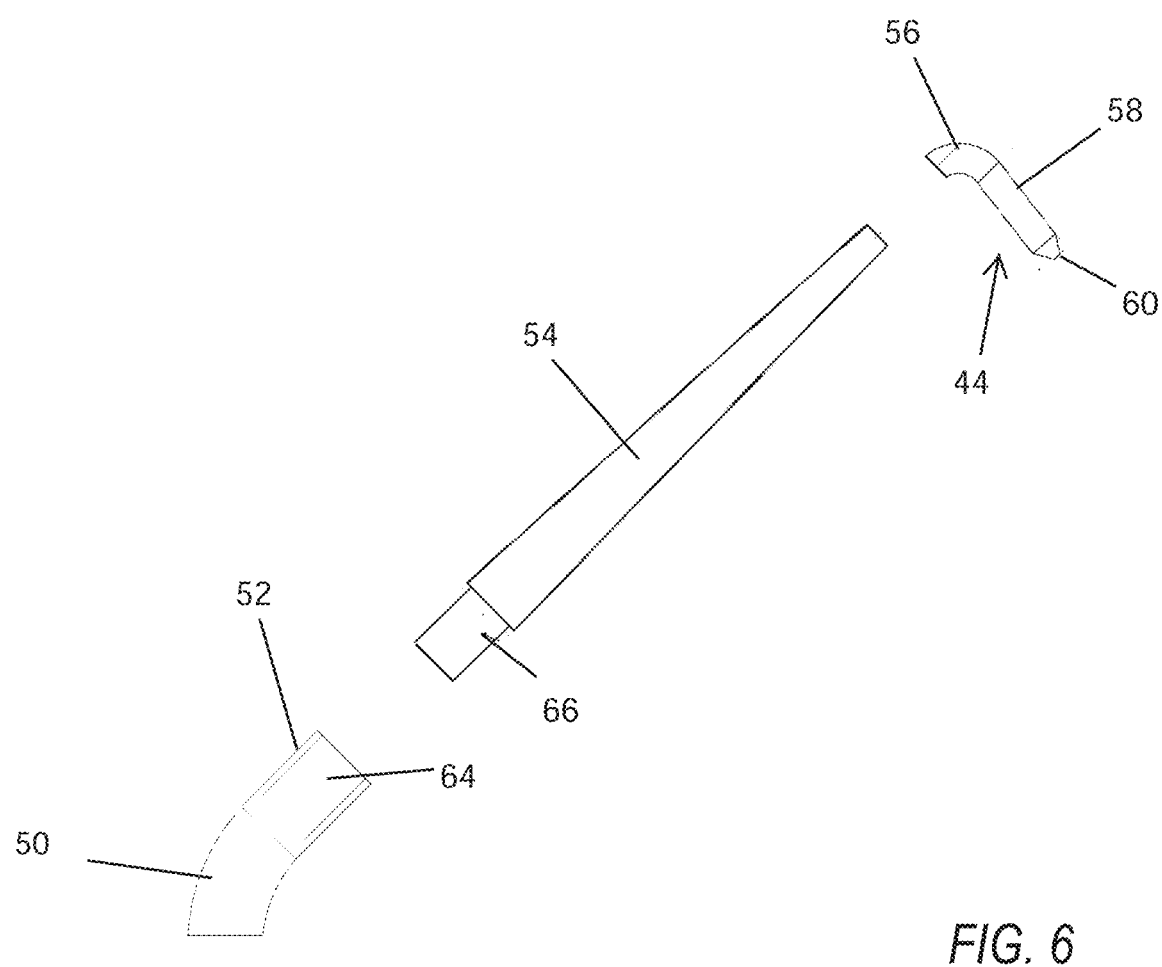
FIG. 6 is a longitudinal sectional view of a base segment of the exemplary endodontic instrument.
Figure 5:
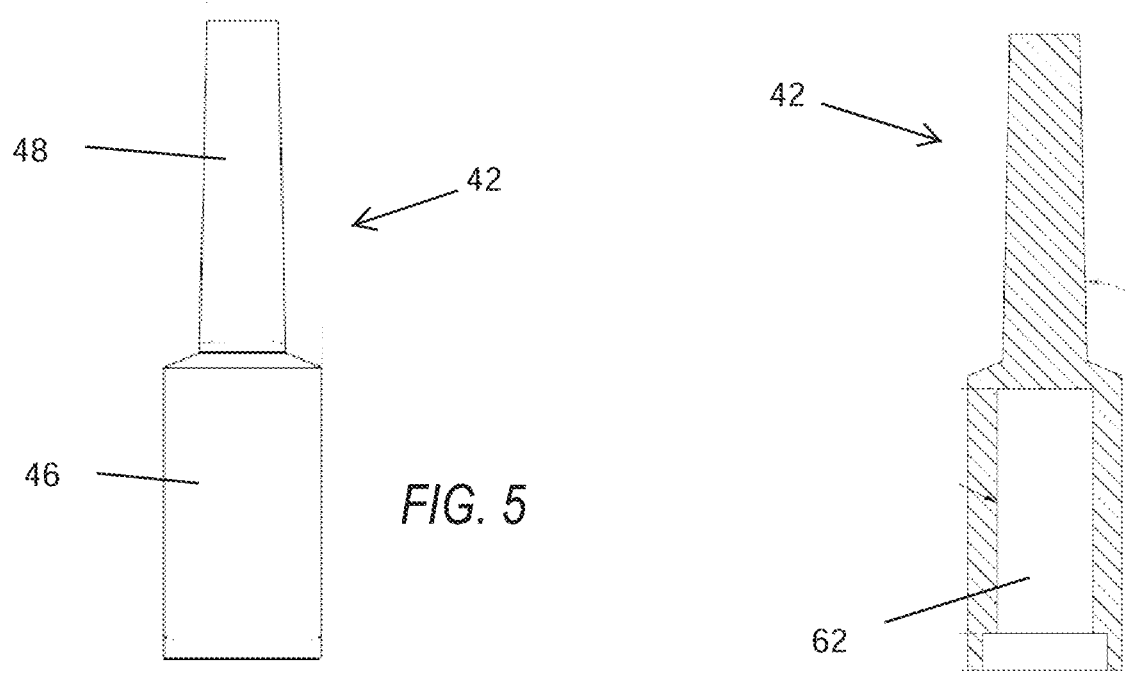
FIG. 5 is an exploded view showing different segments of the exemplary endodontic instrument.

FIG. 5 is an exploded view showing the different segments of the exemplary endodontic instrument 40, while FIG. 6 is a longitudinal sectional view of the proximal base 42. The base 42 desirably includes a central cavity 62 open to its proximal end for receiving a corresponding male projection of an actuating device for generating ultrasonic vibrations. The cavity 62 may be internally threaded, or may be sized to closely receive the male projection in an interference fit. Various ultrasonic generators may be used, such as the Satelec P5 piezoelectric ultrasonic unit from Dentsply Tulsa Dental (Dentsply Sirona of York, Pa.).

The segments are desirably firmly attached together to avoid relative vibrational movement. For instance, the proximal shaft portion 48 of the base 42 is desirably solid in cross-section, and has a flat distal end which couples to a flat proximal end of the first elbow segment 50. These two pieces may be attached in various ways, such as by mating threads or in a more permanent manner such as with adhesive or welding.

The swivel segment 52 defines an inner bore 64 which receives a short stepped-down shaft stub 66 on a proximal end of the distal shaft segment 54. The swivel segment 52 and distal shaft segment 54 are firmly coupled together while permitting relative swiveling about their common central axis. For example, the shaft stub 66 may closely fit within the inner bore 64 and be secured therein using a staking connection method. Staking is the process of connecting two components by creating an interference fit between the two pieces. One workpiece has a hole in it while the other has a boss that fits within the hole. The boss is very slightly undersized so that it forms a slip fit. A staking punch is then used to compress the boss axially and expand the boss radially so as to form an interference fit between the workpieces. This forms a permanent joint. Staking allows the swivel to take place without one piece becoming loose when turned/swiveled.

In a preferred embodiment, the instrument provides indexed rotation such that the distal tip nominally stops at evenly spaced angular rotations. In particular, the connection between the swivel segment 52 distal shaft segment 54 provides the indexed swivel. In other words, the distal shaft segment 54 to which the bent tip 44 attaches maybe swiveled at incremental angles of rotation. For example, the connection may be such that the bent tip 44 may be swiveled 360° around while clicking into place at intervening intermediate angles, such as 90°, and more preferably at least 15°. The incremental angles of rotation may be any angle 0° to 360°. Being able to click the bent tip 44 into various positions and have it be nominally restrained by the connection is a great benefit to the endodontist who can then rotate the bent tip 44 to desired angle for various teeth and procedures.

This swiveling along the length of the endodontic instrument 40, and in particular just distal to the first elbow segment 50, allows a single instrument to be used in multiple quadrants and on different teeth no matter what position the teeth are in. One benefit is in the fact that the instrument can be rotated and used in another tooth in another location in the mouth. It should be noted that a particular construction of the instrument may vary while still featuring the swivel aspect.

Continuing along the instrument 40, the distal shaft segment 54 of the flat distal end which attaches to a proximal end of the second elbow segment 56. Again, the attachment may be via mating threads, or through adhesive or welding.

The material of the various segments of the instrument 40 is preferably the same to enhance smooth propagation of the ultrasonic vibrations therethrough. For instance, the present instrument 40 may be made from stainless steel, a titanium alloy, or a combination of two metals such as stainless steel coated with zirconium nitride.

In use, the active cutting portion of the instrument is used to prep the apical extent of the root end (that's embedded in the bone). The instrument actually goes apically into the root canal from the apical region.

Exemplary specifications of the instrument include the following:

a. 75 degrees double angled ultrasonic instrument b. Between the first and second angles of the instrument, the instrument is able to "swivel" so that the second angle of the instrument can rotate around any degree increments all the way around, 360 degrees. At any degree rotation, the instrument tip can "lock" into place so there is no movement when using the instrument in the ultrasonic unit. This allows the instrument to be used for all quadrants, anterior and posterior teeth without switching out the instrument for another one.

c. Diamond coated cutting tip (approximately 3.5 mm)

e. There will be a separate "wrench-like" instrument that is utilized to actually rotate the "Swivel" piece of the instrument at increments such as 15°, 30°, 45°, 90° or any other desired rotational increment.

Throughout this description, the embodiments and examples shown should be considered as exemplars, rather than limitations on the apparatus and procedures disclosed or claimed.

What is claimed:

1. An endodontic instrument for ultrasonic root end retro-preparation, comprising:
a plurality of segments extending from a proximal base to a bent distal tip, the proximal base having an opening at a proximal end thereof adapted to receive an actuator of an ultrasonic energy generator, the segments being attached together to enable propagation of ultrasonic energy from the proximal base to the distal tip, the segments including a first elbow segment attached to the proximal base and a swivel segment located distal to the first elbow segment, the swivel segment enabling rotation of the bent distal tip relative to the first elbow segment, wherein the segments are made of the same metal, and wherein the plurality of segments define a double-angled shape having a length of between about 1-2 in.

2. The instrument of claim 1, wherein the distal tip may be rotated 360° relative to the first elbow segment.

3. The instrument of claim 2, wherein the instrument provides indexed rotation for the distal tip such that the distal tip nominally stops at evenly spaced angular rotations.

4. The instrument of claim 3, wherein the evenly spaced angular rotations are at least 15°.

5. The instrument of claim 1, wherein the instrument provides indexed rotation for the distal tip such that the distal tip nominally stops at evenly spaced angular rotations.

6. The instrument of claim 1, wherein the first elbow segment defines an angle of between 15-60°.

7. The instrument of claim 6, wherein there is a straight distal shaft extending between the first elbow segment and a second elbow segment, the second elbow segment defining the angle of the bent distal tip and being between 75-110°.

8. The instrument of claim 7, wherein the first elbow segment defines an angle of about 44°, and the angle defined by the second elbow segment is about 75°.

9. The instrument of claim 7, wherein a length of the bent tip that projects beyond the second elbow segment is in the range of about 0.08-0.15 in.

10. The instrument of claim 1, wherein the plurality of segments of the instrument are made from a material selected from group consisting of stainless steel, a titanium alloy, and stainless steel coated with zirconium nitride.

11. An endodontic instrument for ultrasonic root end retro-preparation, comprising:
a plurality of segments extending from a proximal base to a distal tip, the segments being connected together in series and including elements starting from the proximal base and extending in series to the distal tip:
  i. a straight coupling member forming a part of the proximal base and defining a base axis, the coupling member having an opening at a proximal end thereof adapted to receive an actuator of ultrasonic energy generator,
  ii. a straight proximal shaft portion forming a part of the proximal base and having a diameter less than a diameter of the coupling member, the proximal shaft portion being aligned along the base axis,
  iii. a first elbow segment defining a primary bend of the instrument having an angle of between 15-60°,
  iv. a straight swivel segment,
  v. a straight distal shaft segment aligned along a common central axis with the swivel segment and defining a distal axis,
  vi. a second elbow segment defining a secondary bend of the instrument having an angle of between 75-115°,
  vii. the distal tip including a straight segment defining a tip axis and a pointed distal end,
the segments being attached together to enable propagation of ultrasonic energy from the proximal base to the distal tip, and wherein the swivel segment enables 360° rotation of the distal tip about the common central axis.

12. The instrument of claim 11, wherein the instrument provides indexed rotation for the distal tip such that the distal tip nominally stops at evenly spaced angular rotations.

13. The instrument of claim 12, wherein the evenly spaced angular rotations are at least 15°.

14. The instrument of claim 11, wherein the primary bend of the instrument has an angle of about 44°, and the secondary bend of the instrument has an angle of about 75°.

15. The instrument of claim 11, wherein a length of the bent distal tip that projects beyond the second elbow segment is in the range of about 0.08-0.15 in.

16. The instrument of claim 11, wherein the plurality of segments of the instrument are made from a material selected from group consisting of stainless steel, a titanium alloy, and stainless steel coated with zirconium nitride.

17. The instrument of claim 11, wherein a total height of the instrument as measured along the base axis is between about 1-2 in.

18. The instrument of claim 17, wherein a total width of the instrument as measured perpendicular to the base axis is between about 0.6-0.7 in.

19. The instrument of claim 11, wherein the swivel segment and the distal shaft segment are firmly coupled together while permitting relative swiveling about the common central axis using a staking connection.

20. A method including performing an ultrasonic root end retro-preparation using the instrument of claim 11, including resection of a portion of an apical end of a root canal, inserting the distal tip of the instrument into the root canal, transmitting ultrasonic vibrations to the instrument so as to clean out infected material within the root canal, removing the distal tip from the root canal, swiveling the distal tip, re-inserting the distal tip of the instrument into the root canal and repeating the step of transmitting ultrasonic vibrations to further clean out infected material within the root canal.

\* \* \* \* \*